(12) United States Patent
Boucneau et al.

(10) Patent No.: US 12,693,774 B2
(45) Date of Patent: Jul. 28, 2026

(54) METHODS AND SYSTEMS FOR MEDICAL IMAGE RENDERING

(71) Applicant: GE Precision Healthcare LLC, Waukesha, WI (US)

(72) Inventors: Tanguy Boucneau, Versailles (FR); Marine Loth, Noisy le Roi (FR); Romane Amice, Paris (FR); Louise Lelievre, Clamart (FR); Cedric Castanier, Guyancourt (FR); Adeline Digard Bahuon, Bonnelles (FR)

(73) Assignee: GE Precision Healthcare LLC, Waukesha, WI (US)

( * ) Notice: Subject to any disclaimer, the term of this patent is extended or adjusted under 35 U.S.C. 154(b) by 324 days.

(21) Appl. No.: 18/496,782

(22) Filed: Oct. 27, 2023

(65) Prior Publication Data
US 2025/0138709 A1 May 1, 2025

(51) Int. Cl.
| | |
|---|---|
| *G06F 3/048* | (2013.01) |
| *G06F 3/04812* | (2022.01) |
| *G06F 3/04842* | (2022.01) |
| *G06T 7/00* | (2017.01) |
| *G06T 19/00* | (2011.01) |
| *G16H 15/00* | (2018.01) |
| *G16H 30/40* | (2018.01) |

(52) U.S. Cl.
CPC ...... *G06F 3/04842* (2013.01); *G06F 3/04812* (2013.01); *G06T 7/0012* (2013.01); *G06T 19/00* (2013.01); *G16H 15/00* (2018.01); *G16H 30/40* (2018.01); *G06T 2200/04* (2013.01); *G06T 2200/24* (2013.01); *G06T*

*2207/20021* (2013.01); *G06T 2207/20104* (2013.01); *G06T 2207/30096* (2013.01); *G06T 2207/30101* (2013.01); *G06T 2210/41* (2013.01)

(58) Field of Classification Search
CPC . G06F 3/04842; G06F 3/04812; G16H 15/00; G16H 30/40; G06T 7/0012; G06T 19/00
See application file for complete search history.

(56) References Cited

U.S. PATENT DOCUMENTS

| | | |
|---|---|---|
| 7,492,967 B2 | 2/2009 | Toki |
| 8,625,869 B2 | 1/2014 | Harder |
| 8,693,752 B2 | 4/2014 | Claes |

(Continued)

OTHER PUBLICATIONS

International Application No. PCT/US2024/045202 filed on Sep. 4, 2024, International Search Report and Written Opinion issued Dec. 2, 2024, 16 pages.

*Primary Examiner* — David Phantana-angkool

(57) ABSTRACT

A system for rendering medical images is described herein. The system can include a processor configured to obtain, using a three-dimensional cursor, a selection of a region of interest from a three-dimensional (3D) medical image. The processor can also detect a three-dimensional cursor setting for the region of interest, the three-dimensional cursor setting indicating at least a rendering setting for the region of interest. Furthermore, the processor can modify a user interface comprising the 3D medical image with the three-dimensional cursor setting applied inside the region of interest, wherein movement of the three-dimensional cursor causes a selection of a second region in the 3D medical image, wherein the second region is displayed with the rendering setting.

20 Claims, 9 Drawing Sheets

(56)    References Cited

U.S. PATENT DOCUMENTS

| | | | | |
|---|---|---|---|---|
| 10,070,839 | B2 * | 9/2018 | Westerhoff | G16H 50/20 |
| 10,893,844 | B1 * | 1/2021 | Douglas | A61B 90/39 |
| 12,033,296 | B2 * | 7/2024 | Scapel | G06T 11/60 |
| 12,287,913 | B2 * | 4/2025 | Rickwald | G06F 3/017 |
| 12,324,680 | B1 * | 6/2025 | Lochner | A61B 5/444 |
| 12,333,087 | B2 * | 6/2025 | Douglas | G06F 3/04815 |
| 12,379,834 | B2 * | 8/2025 | Triverio | G06F 3/04847 |
| 12,399,932 | B1 * | 8/2025 | Barve | G06T 19/00 |
| 12,482,161 | B2 * | 11/2025 | Scapel | A63F 13/655 |
| 2016/0026266 | A1 | 1/2016 | Douglas | |
| 2017/0090739 | A1 * | 3/2017 | Kozuka | G16H 30/20 |
| 2020/0167917 | A1 * | 5/2020 | Douglas | A61B 6/463 |
| 2023/0343053 | A1 * | 10/2023 | Scapel | G06T 11/60 |
| 2024/0372968 | A1 * | 11/2024 | Rickwald | G06V 40/171 |
| 2025/0272938 | A1 * | 8/2025 | Scapel | G06F 3/0482 |

* cited by examiner

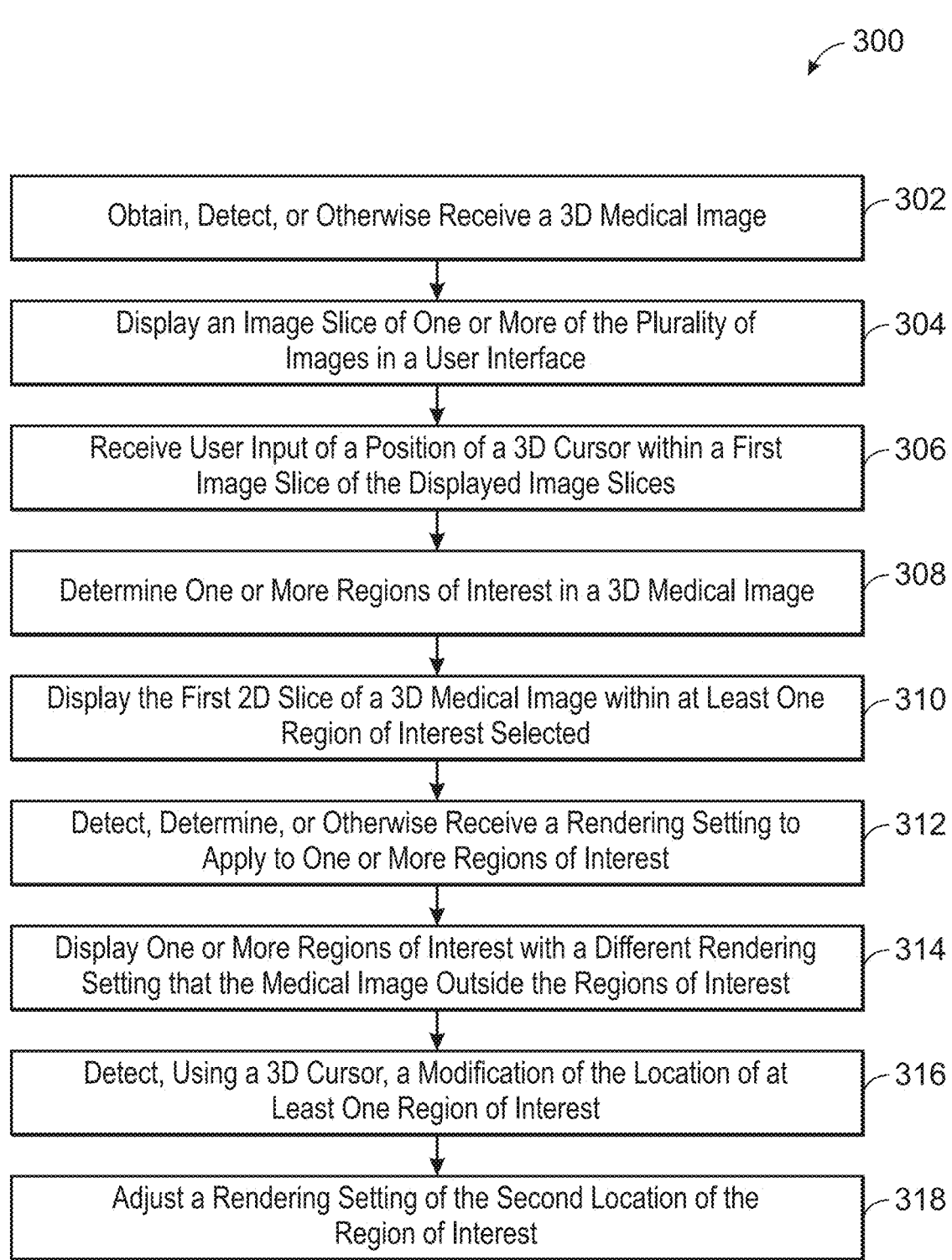

300

Obtain, Detect, or Otherwise Receive a 3D Medical Image — 302

Display an Image Slice of One or More of the Plurality of Images in a User Interface — 304

Receive User Input of a Position of a 3D Cursor within a First Image Slice of the Displayed Image Slices — 306

Determine One or More Regions of Interest in a 3D Medical Image — 308

Display the First 2D Slice of a 3D Medical Image within at Least One Region of Interest Selected — 310

Detect, Determine, or Otherwise Receive a Rendering Setting to Apply to One or More Regions of Interest — 312

Display One or More Regions of Interest with a Different Rendering Setting that the Medical Image Outside the Regions of Interest — 314

Detect, Using a 3D Cursor, a Modification of the Location of at Least One Region of Interest — 316

Adjust a Rendering Setting of the Second Location of the Region of Interest — 318

FIG. 3

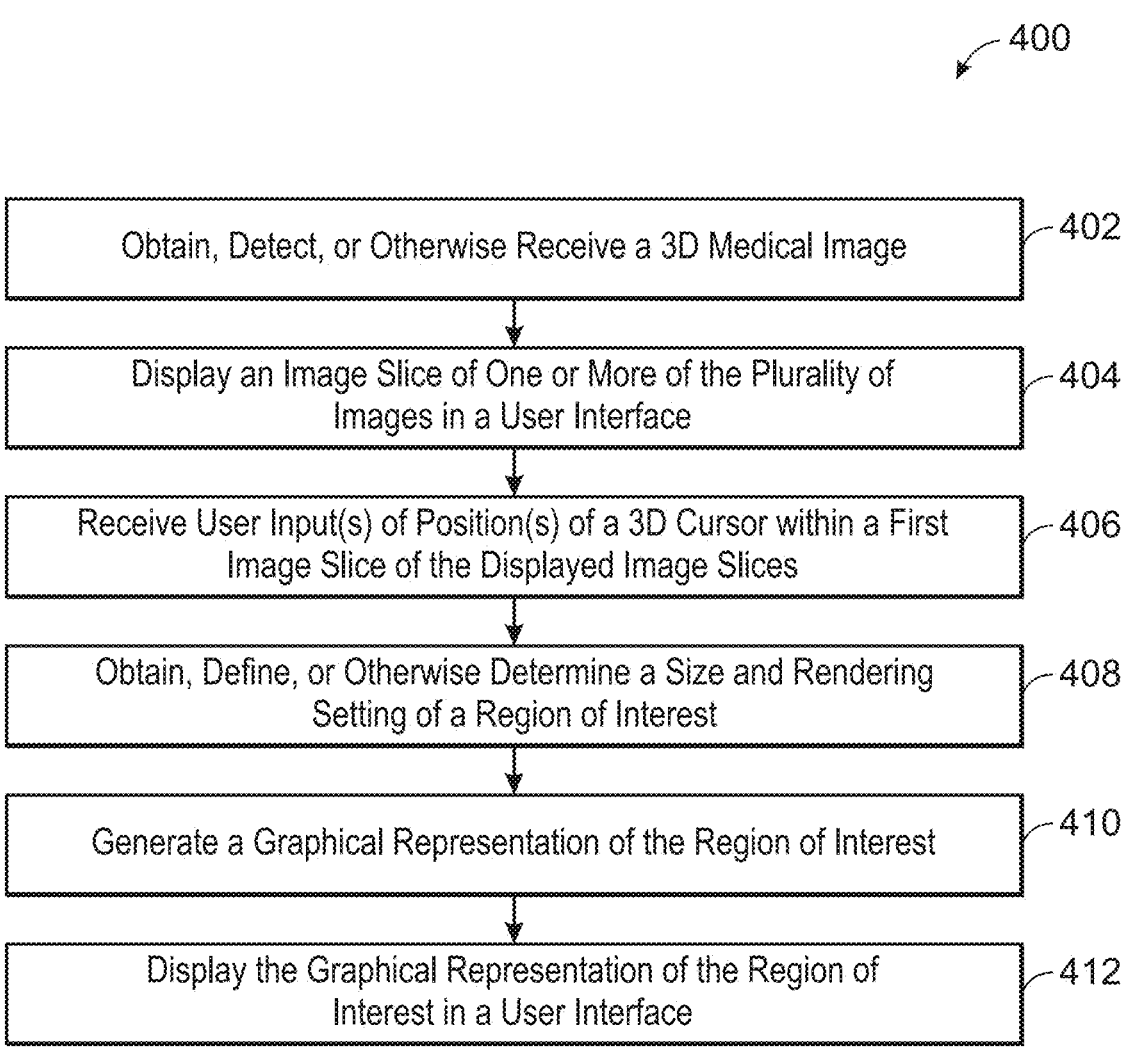

400

Obtain, Detect, or Otherwise Receive a 3D Medical Image — 402

Display an Image Slice of One or More of the Plurality of Images in a User Interface — 404

Receive User Input(s) of Position(s) of a 3D Cursor within a First Image Slice of the Displayed Image Slices — 406

Obtain, Define, or Otherwise Determine a Size and Rendering Setting of a Region of Interest — 408

Generate a Graphical Representation of the Region of Interest — 410

Display the Graphical Representation of the Region of Interest in a User Interface — 412

FIG. 4

METHODS AND SYSTEMS FOR MEDICAL IMAGE RENDERING

FIELD

Techniques disclosed herein relate to image processing, and more particularly to image rendering of three-dimensional medical images.

BACKGROUND

Clinical decisions may be derived from analysis of any number of sets of data. In the radiology domain, this can involve analysis of regions of interest from medical image data, which may include 2D or 3D medical images, such as images of organs (kidney, liver, spleen, etc.), blood vessels, bones, and the like. In some examples, medical image analysis can be performed at the request of a clinician for a specific purpose, which can include detection, assessment, and/or monitoring progression of anatomical abnormalities like lesions, tumors, aneurysms, atrophies, and stenosis of arteries, among others.

Visualization tools can enable accessing regions of interest of medical image data and performing the desired analysis. A rendering process can be employed to separate the rendering of regions of interest so as to improve a user interface for visualizing, detecting, assessing, and monitoring various anatomical abnormalities.

BRIEF DESCRIPTION

In one example, a system for rending medical images can include a processor that can be configured to obtain, using a three-dimensional cursor, a selection of a region of interest from a three-dimensional (3D) medical image. The processor can also be configured to detect a three-dimensional cursor setting for the region of interest, the three-dimensional cursor setting indicating at least a rendering setting for the region of interest. Additionally, the processor can be configured to modify a user interface comprising the 3D medical image with the three-dimensional cursor setting applied inside the region of interest. In some examples, movement of the three-dimensional cursor causes a selection of a second region in the 3D medical image, wherein the second region is displayed with the rendering setting.

In some examples, a method for rendering medical images can include obtaining, using a three-dimensional cursor, a selection of a region of interest from a three-dimensional (3D) medical image and detecting a three-dimensional cursor setting for the region of interest, the three-dimensional cursor setting indicating at least a rendering setting for the region of interest. The method can also include modifying a user interface comprising the 3D medical image with the three-dimensional cursor setting applied inside the region of interest, wherein movement of the three-dimensional cursor causes a selection of a second region in the 3D medical image, wherein the second region is displayed with the rendering setting.

In some examples, a non-transitory computer readable medium for rendering medical images can include a plurality of instructions that, in response to execution by a processor, cause the processor to obtain, using a three-dimensional cursor, a selection of a region of interest from a three-dimensional (3D) medical image. The plurality of instructions can also cause the processor to detect a three-dimensional cursor setting for the region of interest, the three-dimensional cursor setting indicating at least a rendering setting for the region of interest, the rendering setting comprising a maximum intensity projection, a minimum intensity projection, or an average intensity projection. Additionally, the plurality of instructions can cause the processor to modify a user interface comprising the 3D medical image with the three-dimensional cursor setting applied inside the region of interest, wherein movement of the three-dimensional cursor causes a selection of a second region in the 3D medical image, wherein the second region is a cylindrical selection displayed with the rendering setting. It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting examples, with reference to the attached drawings broadly described below:

FIG. 3 shows a flowchart illustrating a method for rendering medical imaging data according to an example of the disclosure.

FIG. 4 shows a flowchart illustrating a method for generating a graphical representation of a region of interest according to an example of the disclosure.

DETAILED DESCRIPTION

Figure 1:
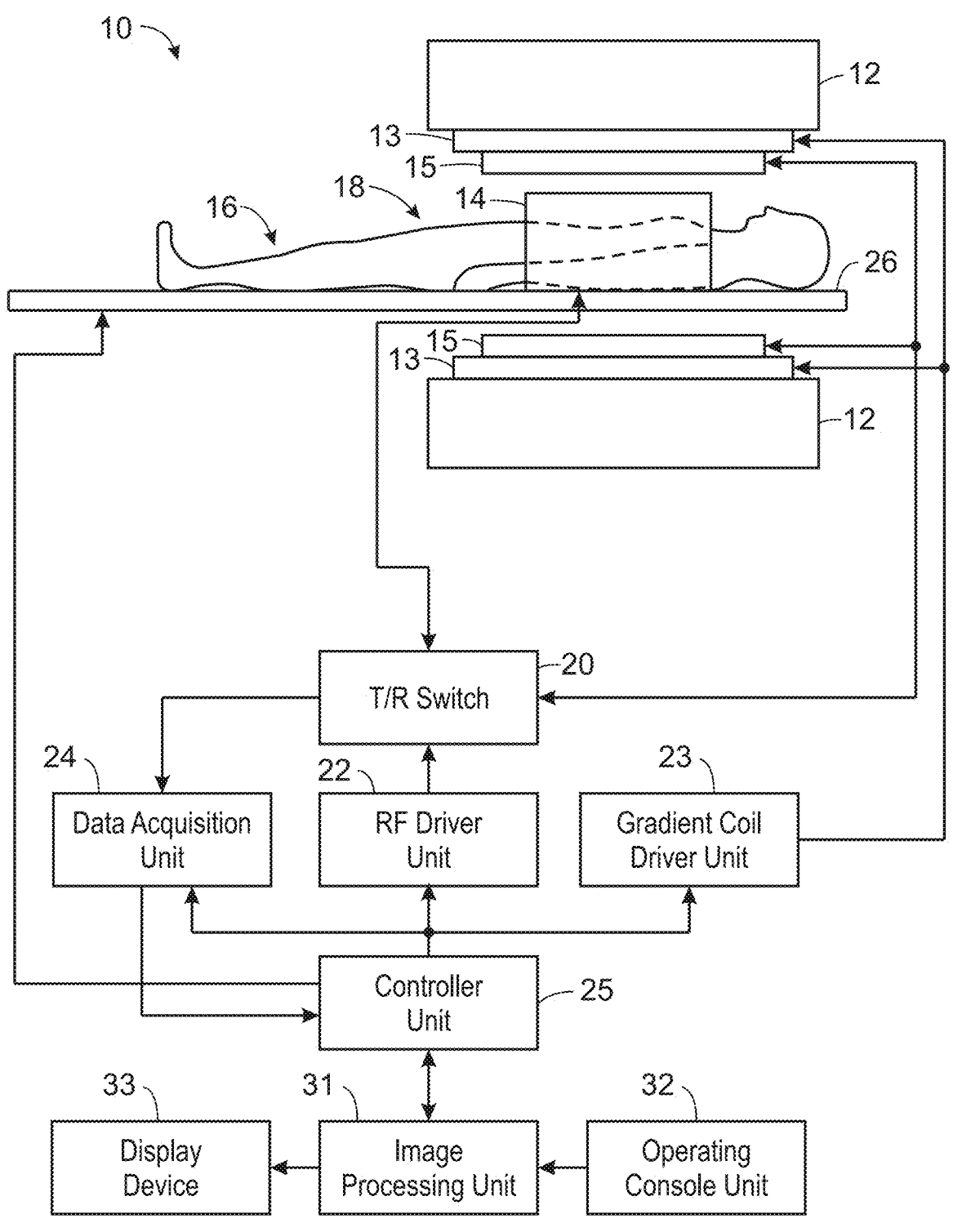
FIG. 1 shows a block diagram of an imaging system according to an example of the disclosure.

The following description relates to various techniques, methods, non-transitory computer-readable media, and systems for the rendering of three-dimensional (3D) medical image data. In some examples, techniques described herein provide a three-dimensional (3D) cursor configured to interactively navigate medical imaging data, provide visualization features for regions of interest, and enable determining regional measurements in medical images. The 3D cursor described can be controllable via a user interface to select a 3D region of interest (ROI). The techniques herein can provide advanced views for various rendering settings, such as maximum intensity projections, minimum intensity projections, and average intensity projections, among others. Additionally, techniques herein can include features integrated into user interfaces that support defining regions inside regions of interest from which statistics can be measured and displayed in graphs, or any other suitable visualization of a structured set of data.

In some examples, the techniques herein can enable identifying regions of interest for image segmentation as part of image processing, which can group similar regions or segments of a medical image. Image segmentation can include, in some examples, partitioning a digital image into distinct regions or components. For example, partitioning a digital image can include identifying image regions or segments, wherein each image region or segment can be a collection of pixels or voxels. Image partitioning can be utilized in order to simplify or change the representation of an image into data or another image, among others, that can be more meaningful and easier to analyze.

In some examples, image segmentation can be used in a variety of applications, including in medical imaging. During analysis of medical image data, which can be two-dimensional (2D), 3D, or in some examples, 3D with multiple volumes (e.g., multi-parametric imaging data or multi-phase imaging data), it may be useful to apply segmentation to the medical image data in order to allow for easier characterization of certain anatomical features (e.g., organs, lesions, etc.) by a referring physician for diagnosis, analysis, and the like. Segmentation is implementable on medical images captured using a variety of modalities, including magnetic resonance imaging (MRI), computing tomography (CT), positron emission tomography (PET), ultrasound, and more.

Techniques herein can also be utilized with multi-volume imaging data, as is generated by multi-parametric and/or multi-phase imaging methods, which increase available data of regions of interest. The multi-volume imaging data can demand individual segmentation for each sequence or phase despite being of the same 3D imaging data. Multi-parametric imaging data, such as multi-parametric MRIs, CTs, ultrasounds, and the like, may combine a plurality of imaging parameters (e.g., sequences) for a set of 3D medical imaging data. For example, a multi-parametric MRI may include data of multiple sequences, such as a T1-weighted sequence, a T2-weighted sequence, a T1 contrast enhanced (TICE) sequence, a fluid attenuated inversion recovery (FLAIR) sequence, a diffusion weighted imaging (DWI) sequence, among many others. Multi-phase imaging data include multiple images taken of a target anatomy at various points in time, typically as intravenous contrast dye moves through the circulatory system. As an example, a multi-phase liver CT may include a non-contrasted phase image, an arterial phase image (e.g., late arterial phase), a portal venous phase image, and a delayed phase image, wherein each image is acquired at different times when the contrast dye is at a particular enhancement for a specified area. For example, for the arterial phase, peak aortic attenuation may be seen with minimal liver enhancement while, for the portal venous phase, peak liver parenchyma and portal and hepatic vein enhancement may be seen.

In this way, multi-volume imaging data that includes multiple image volumes of the same target anatomy with different parameters or at different times may provide a fourth dimension to 3D imaging data, whereby a lesion or other region of interest may be imaged either in various manners (e.g., sequences of multi-parametric imaging) and/or at various times (e.g., phases of multi-phase imaging), providing increased information and imagery of the region of interest. As noted, in order to segment and/or annotate multi-volume imaging data, annotation and segmentation may be done for each of the volumes individually, as in some examples a lesion or region of interest that is to be segmented may appear differently in different volumes, therefore consuming increased amounts of time for a user as well as increased processing power.

In some examples disclosed herein, images of 3D multi-volume, e.g., multi-parametric and/or multi-phase, imaging data can be rendered for a user to identify regions of interest, provide annotation inputs, or the like. A position of a user cursor within a first 2D slice of a first volume of the 3D multi-volume imaging data may be located and a region of interest can be identified within the 3D medical imaging data. In some examples, the region of interest can be a spherical region, a cylindrical region, or any other suitable geometric representation of a 2D or 3D region within the medical imaging data.

Thus, technical advantages of the techniques described herein can include displaying advanced views or renderings of regions of interest using a modified user interface component. The modified user interface component provides a user with a feature for quickly viewing a region of interest with a different rendering setting or representation, without losing focus on the medical image for review. Other technical advantages of the present techniques herein can include interactively obtaining a measurement statistic within a region of interest. This provides a feature that can quickly obtain and display measurement data within a region of interest along time in a graph for a temporal sequence of images. A region of interest statistic measurement can be, in some examples, more robust to spatial noise compared to the image signal obtained from one single voxel, which leads to a more reliable structured set of data.

The technical effect of the methods and systems provided herein is, in some examples, that imaging data can be rendered or processed differently within one or more regions of interest. For example, imaging data within an identified, obtained, or otherwise received region of interest can be rendered using a different setting than the imaging data outside of the region of interest. In some examples, any number of regions of interest can be provided using a user interface, wherein each region of interest can be rendered with a shared or different rendering setting. The techniques herein have the technical effect or technical advantage of reducing processing time for the medical imaging data by adjusting the rendering of data within one or more regions of interest without modifying the rendering setting for the medical imaging data outside of the one or more regions of interest. Furthermore, techniques herein have a technical effect or technical advantage of reducing memory usage for a user interface used for viewing medical imaging data by temporarily providing a region of interest with a different rendering setting without storing copies of the medical imaging data in memory with different rendering settings applied to the entire medical imaging data.

Further, generation or rendering of regions of interest within medical imaging data as described herein can be performed in real-time. For example, rendering settings within one or more regions of interest in the medical imaging data can be modified in real-time as rendering inputs (e.g., mouse clicks or drags) are detected within a user interface displaying imaging data. In this way, the methods and systems herein may reduce time spent by the user in reviewing, analyzing, and rendering medical imaging data as well as increasing processing efficiency.

Figure 2:
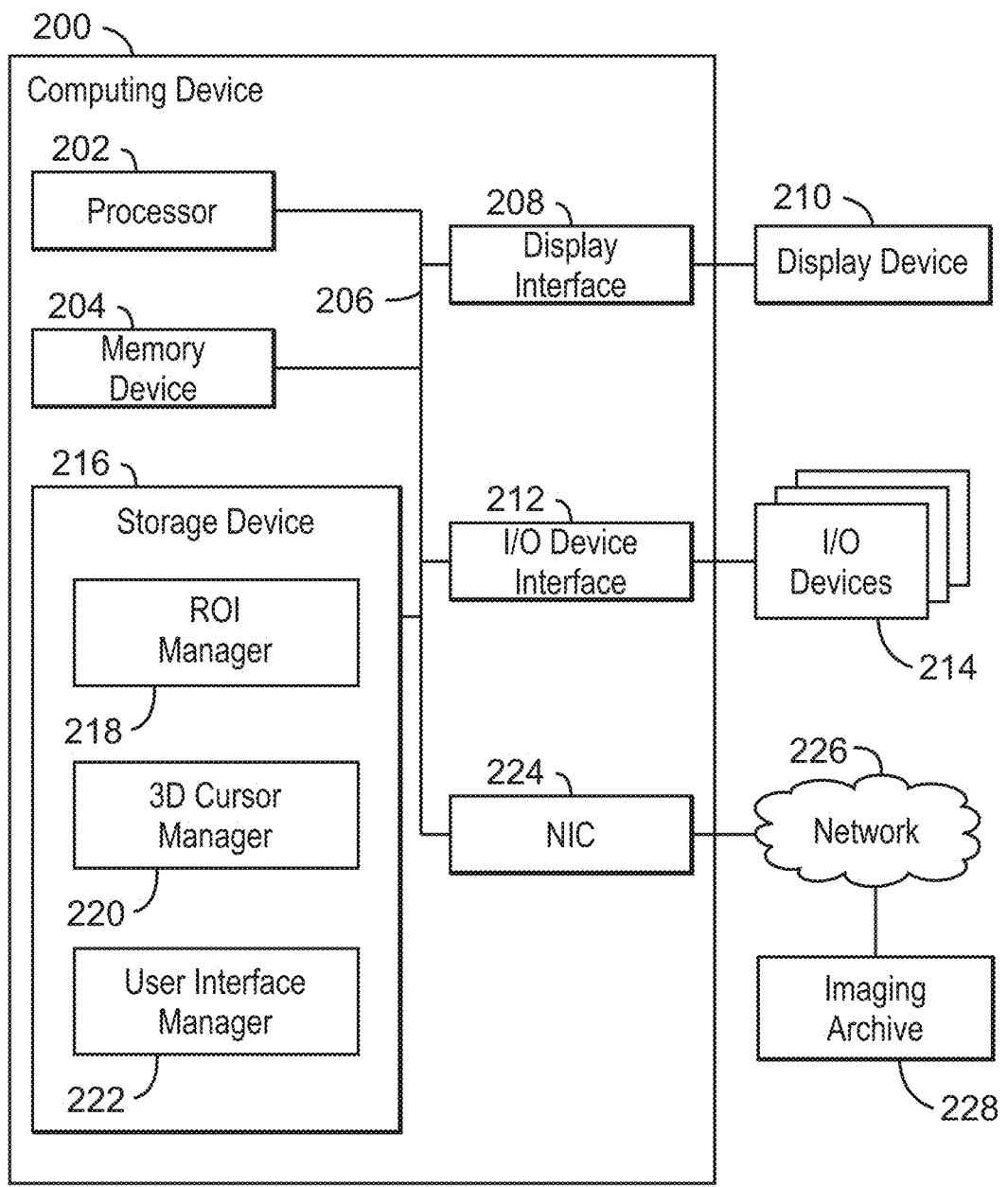
FIG. 2 shows a block diagram of a computing device according to an example of the disclosure.
Figure 5:
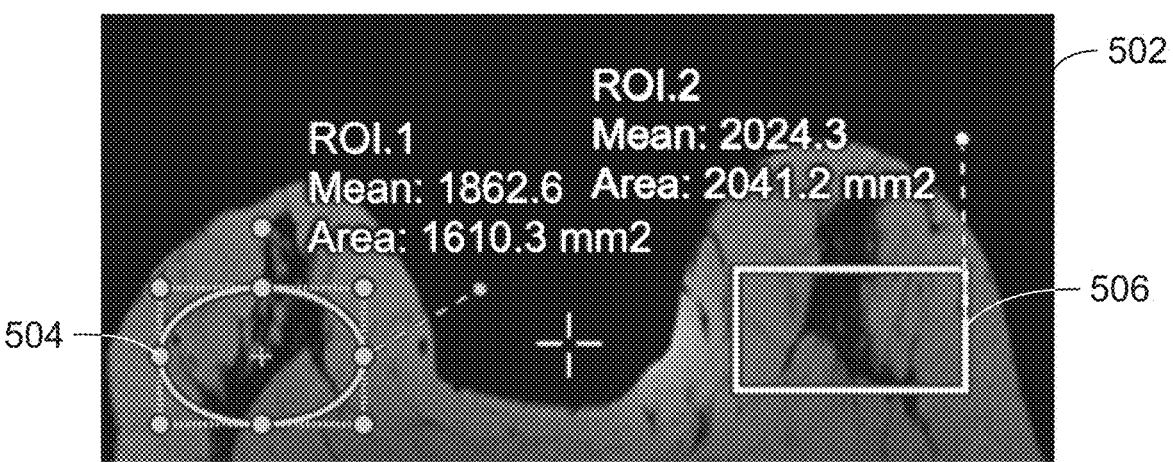
FIG. 5 shows an example image from a multi-volume imaging dataset of a patient according to an example of the disclosure.

Techniques of the present disclosure will now be described, by way of example, with reference to the figures. FIG. 1 illustrates an example imaging system that may be used to acquire 3D multi-volume imaging data. FIG. 2 shows a block diagram of a computing device that may be a part of or otherwise communicatively coupled to the imaging system. FIG. 3 shows a flowchart illustrating a method for rendering medical imaging data. FIG. 4 shows a flowchart illustrating a method for generating a graphical representation of a region of interest. FIG. 5 shows an example image of a multi-volume imaging dataset of a patient. FIGS. 6-9 show example images of a user interface for rendering medical images. FIGS. 10A and 10B depict graphical representations of medical imaging data from a region of interest.

Turning now to FIG. 1, an illustration of an example imaging system as may be used to generate 3D multi-volume imaging data is shown. As an example, an MRI system 10 includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient bed or table 26, an image processing unit 31, an operating console unit 32, and a display device 33. In some examples, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI system 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI system 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some examples, the RF coil unit 14 may transmit the RF pulse and receive the MR signal. In other examples, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the image processing unit 31 and the display device 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The image processing unit 31 includes a computing device and a recording medium on which a program to be executed by the computing device to perform predetermined data processing is recorded. The image processing unit 31 is connected to the controller unit 25 and performs data processing based on control signals received from the controller unit 25. The image processing unit 31 is also connected to the data acquisition unit 24 and generates spectrum data by applying various image processing operations to the magnetic resonance signals output from the data acquisition unit 24.

The display device 33 may display one or more images within a GUI on the display screen of the display device based on control signals received from the controller unit 25. The display device 33 displays, for example, an image regarding an input item about which the operator inputs operation data from the operating console unit 32. The display device 33 also displays a two-dimensional (2D) slice image or three-dimensional (3D) image of the subject 16 generated by the image processing unit 31.

The MRI system 10 may be configured for multi-volume imaging, e.g., multi-parametric and/or multi-phase imaging, wherein multiple imaging sequences and/or phases are imaged during a single imaging session. Resultant MRI imaging data may include images from each of the imaged sequences and/or phases, wherein the MRI imaging data is subdivided into specified sequences and/or phases. Each of the specified sequences and/or phases may define a plurality of 2D slices thereof, each of the 2D slices particular to a z-coordinate of the MRI imaging data. A z-coordinate may therefore define a plurality of 2D slices, one from each of the specified sequences and/or phases.

Though an MRI system is described by way of example, it should be understood that the present techniques may be applied to images acquired using other imaging systems capable of multi-parametric, multi-phase, or other type of multi-volume imaging, such as CT, tomosynthesis, PET, ultrasound, and so forth. The present discussion of an MRI imaging modality is provided merely as an example of one suitable imaging modality.

FIG. 2 is a block diagram of an example of a computing device that can render medical imaging data. The computing device 200 may be, for example, a medical imaging system, such as the medical imaging system 100, a CT device, a PET device, an ultrasound device, a hospital monitor, a laptop computer, a desktop computer, a tablet computer, or a mobile phone, among others. The computing device 200 may include a processor 202 that is adapted to execute stored instructions, as well as a memory device 204 that stores instructions that are executable by the processor 202. The processor 202 can be a single core processor, a multi-core processor, a computing cluster, or any number of other configurations. The memory device 204 can include random access memory, read only memory, flash memory, or any other suitable memory systems. The instructions that are executed by the processor 202 may be used to implement a method that can render medical imaging data, as described in greater detail below in relation to FIGS. 3-4.

The processor 202 may also be linked through the system interconnect 206 (e.g., PCI, PCI-Express, NuBus, etc.) to a display interface 208 adapted to connect the computing device 200 to a display device 210. The display device 210 may include a display screen that is a built-in component of the computing device 200. The display device 210 may also include a computer monitor, television, or projector, among others, that is externally connected to the computing device 200. The display device 210 can include light emitting diodes (LEDs), and micro-LEDs, Organic light emitting diode OLED displays, among others.

The processor 202 may be connected through a system interconnect 206 to an input/output (I/O) device interface 212 adapted to connect the computing device 200 to one or more I/O devices 214. The I/O devices 214 may include, for example, a keyboard and a pointing device, wherein the pointing device may include a touchpad or a touchscreen, among others. The I/O devices 214 may be built-in components of the computing device 200, or may be devices that are externally connected to the computing device 200.

In some examples, the processor 202 may also be linked through the system interconnect 206 to a storage device 216 that can include a hard drive, an optical drive, a USB flash drive, an array of drives, or any combinations thereof. In some examples, the storage device 216 can include any suitable applications. In some examples, the storage device 216 can include a region of interest (ROI) manager 218. In some examples, the ROI manager 218 can obtain, using a three-dimensional cursor, a selection of a region of interest from a three-dimensional (3D) medical image. In some examples, the storage device 216 can also include a 3D cursor manager 220 that can detect a three-dimensional cursor setting for the region of interest. The three-dimensional cursor setting can indicate at least a rendering setting for the region of interest. The rendering setting, as referred to herein, can include a maximum intensity projection, a minimum intensity projection, or an average intensity projection, among others, of pixels or voxels within a region of medical imaging data. The storage device 216 can also include, in some examples, a user interface manager 222 that can modify a user interface that includes the 3D medical image with the three-dimensional cursor setting applied inside the region of interest. In some examples, movement of the three-dimensional cursor causes a selection of a second region in the 3D medical image, wherein the second region is displayed with the rendering setting. FIGS. 6-9, discussed in greater detail below, provide an example of a selection of a second region in a 3D medical image with a 3D cursor.

In some examples, a network interface controller (also referred to herein as a NIC) 224 may be adapted to connect the computing device 200 through the system interconnect 206 to a network 226. The network 226 may be a cellular network, a radio network, a wide area network (WAN), a local area network (LAN), or the Internet, among others. The network 226 can enable data, such as alerts, among other data, to be transmitted from the computing device 200 to remote computing devices, remote display devices, and the like. For example, the network 226 may enable remote devices (e.g., imaging archive 228, among others) to generate or modify user interfaces by rendering any number of regions of interest in a medical imaging data set with a different rending setting, among other features.

It is to be understood that the block diagram of FIG. 2 is not intended to indicate that the computing device 200 is to include all of the components shown in FIG. 2. Rather, the computing device 200 can include fewer or additional components not illustrated in FIG. 2 (e.g., additional memory components, embedded controllers, additional modules, additional network interfaces, etc.). Furthermore, any of the functionalities of the ROI manager 218, 3D cursor manager 220, or user interface manager 222 may be partially, or entirely, implemented in hardware and/or in the processor 202. For example, the functionality may be implemented with an application specific integrated circuit, logic implemented in an embedded controller, or in logic implemented in the processor 202, among others. In some examples, the functionalities of the ROI manager 218, 3D cursor manager 220, or user interface manager 222 can be implemented with logic, wherein the logic, as referred to herein, can include any suitable hardware (e.g., a processor, among others), software (e.g., an application, among others), firmware, or any suitable combination of hardware, software, and firmware.

In some examples, the computing device 200 may be incorporated into an imaging system, such as the MRI system 10. For example, the computing device 200 may be the image processing unit 31 of the MRI system 10. However, in other examples, the computing device 200 may be disposed at a device (e.g., a server, edge device, etc.) communicably coupled to the imaging system via wired and/or wireless connections. In some examples, at least a portion of computing device 200 may be disposed at a separate device (e.g., a workstation) which can receive images from the imaging system or from a storage device which stores the images generated by the imaging system and/or other additional imaging systems.

In addition to the images directly provided by the computing device 200, images may be further sourced from an imaging archive 228 communicatively coupled to the computing device 200. The imaging archive 228 may comprise, for example, a picture archiving and communication system (PACS), a vendor neutral archive (VNA), or other suitable medical image database. The medical imaging archive may be hosted on a remote server configured to allow the computing device 200 to access the plurality of medical images and patient data hosted thereon. In some examples, the plurality of medical images stored in the imaging archive 228 may be of different types, for example MRI images, CT images, or ultrasound images, which can be stored in the imaging archive 228 for one or more patients.

Turning now to FIG. 3, a flowchart illustrating a method 300 for rendering medical imaging data is shown. The method 300 will be described with relation to the systems depicted in FIGS. 1-2, but it should be understood that similar methods may be used with other systems without departing from the scope of this disclosure. The method 300 may be carried out via instructions stored in non-transitory memory of one or more computing devices. In some examples, the method 300 may be carried out by a computing device (e.g., the computing device 200 that includes the processor 202 of FIG. 2) as well as a set of remote servers, also referred to herein as a cloud computing system, in communication with the computing device. The computing device may be in communication with an imaging archive (e.g., imaging archive 228) or any other suitable remote device or remote data repository.

At 302, the method 300 can include obtaining, detecting, or otherwise receiving a 3D medical image. In some examples, the 3D medical image can include a plurality of images of a 3D multi-volume imaging dataset from an imaging archive or any other suitable device or data repository. The multi-volume imaging dataset may be acquired via an imaging system (e.g., MRI system 10 of FIG. 1a CT device, or any other suitable medical imaging device) configured for acquiring multi-volume data, such as multi-parametric imaging data and/or multi-phase imaging data, among others. In some examples, the multi-volume imaging dataset that is to be processed, segmented, and/or rendered may be selected via user input. For example, a user may select a desired multi-volume imaging dataset to be rendered or processed. The user input can also indicate a request that the selected 3D multi-volume imaging dataset be rendered with one or more regions of interest (e.g., by selecting a segmentation tab, tool, or the like).

The 3D multi-volume imaging dataset may include a plurality of image volumes. In some examples, each image volume can be from a different imaging sequence or phase. In some examples, each of the plurality of image volumes may be partitioned into a plurality of 2D slices. Each of the 2D slices may be specific to a particular coordinate according to an axis in which they were obtained (e.g., a z-coordinate for an axial view). In some examples, the plurality of 2D slices for each of the plurality of image volumes may have the same set coordinates. In other examples, the set of coordinates of the plurality of 2D slices for one or more of the plurality of image volumes may be different from the other pluralities of 2D slices due to sequencing parameters, acquisition parameters, or the like. The plurality of images obtained can be, in some examples, entire imaging volumes.

At 304, the method 300 includes displaying an image slice from a 3D medical image in a user interface. In some examples, the displayed image slice may be a 2D slice. The user interface can be displayed on a display device (e.g., display device 210 of FIG. 2) and may include one or more selectable elements and/or tools through which the user may interact with the images, render regions of interest in the images, annotate the images, or perform other actions. For example, the user interface can include a 3D cursor that, in response to a selection, can enable navigation of a 3D medical image with additional rendering settings or tools. In some examples, a 3D multi-volume imaging dataset may include images obtained from one or more orientations and therefore images may be displayed in one of various views, e.g., an axial view, sagittal view, coronal view, or the like. In some examples, each of the one or more images displayed may be displayed from the same view.

Further, the plurality of images may additionally include images not displayed within the user interface as well as the displayed images. The user interface may, in some examples, include a menu through which the user may select which of the plurality of images are displayed. For example, a 3D multi-parametric imaging dataset may include volumes from a T1 weighted sequence, a T1 weighted contrast enhanced sequence, a FLAIR sequence, a DWI sequence, and a T2 weighted sequence. The detected user input may include a selection, for example, of the T1 weighted sequence, the FLAIR sequence, and the T2 weighted sequence to be displayed within the user interface. The DWI sequence and the T1 weighted contrast enhanced sequence may be stored in transitory and/or non-transitory memory and may be displayed within the user interface upon user selection via a menu. In other examples, each of the plurality of images of the 3D multi-volume imaging dataset may be displayed within the user interface.

At 306, the method 300 can include receiving user input of a position of a 3D cursor within a first image slice of displayed image slices corresponding to a 3D medical image. In some examples, the first image slice may be of a first image volume representing a 3D medical imaging data set. The 3D cursor may be adjustable via user inputs (e.g., movement of a user input device such as a mouse, trackpad, keyboard, or the like) and the position of the 3D cursor may be determined via user input (e.g., a mouse click, keyboard selection, or the like). In some examples, the position of the 3D cursor can be determined relative to the displayed image/2D slice. In some examples, a coordinate system can be predefined for the 3D imaging data set so that the coordinate system may be the same for each of the volumes of the 3D imaging data set. The position of the 3D cursor can be known, calculated, or otherwise obtained within the first image slice. In some examples, if the coordinate system is the same for each of the volumes, the position of the 3D cursor can be transposed to the other of the plurality of images.

At 308, method 300 can include determining one or more regions of interest in a 3D medical image. In some examples, the one or more regions can be determined using any suitable machine learning technique, obtained by user input at the position of the 3D cursor, or the like. The regions of interest can represent any suitable anatomical abnormality in a medical image such as lesions, stenosis of an artery, or tumors, among others. In some examples, a drag-and-drop selection applied using a 3D cursor can select a 2D or 3D region of interest. A size of the 2D or 3D region of interest can be identified or selected in response to a drag-and-drop operation applied with a 3D cursor to orthogonal bars of the 3D cursor, or the like.

In some examples, more than one position of the 3D cursor can be determined for annotating or rendering an image. For example, multiple positions of the 3D cursor can be determined as the 3D cursor moves from an initial position around a region of interest. One or more positions can be defined along a line, wherein the first position is an initial position of the 3D cursor when an initial user input is received (e.g., a mouse click). One or more second positions can be defined or determined (e.g., by dragging with the mouse clicked) until the initial user input is released (e.g., releasing the mouse click). The user inputs defining the position of the user cursor may be annotation inputs, region of interest, or the like.

In some examples, the method 300 can include automatically positioning the three-dimensional cursor at the region of interest with a predetermined depth, wherein the region of interest represents a cylindrical region in the 3D medical image. In some examples, a diameter of a region of interest can be changed or modified without increasing or decreasing a depth of the rendering.

At 310, method 300 can include displaying the first 2D slice of a 3D medical image within at least one region of interest selected. In some examples, the region of interest and the 2D slice of a 3D medical image can be initially displayed with shared settings, such as a shared focus setting, rendering setting, and the like. As discussed above, a size of the region of interest can be detected or obtained by any suitable user input, such as a click and drag with a mouse, among others. In some examples, a 3D cursor can be used to select a region of interest. The selected region of interest can be displayed with any suitable predetermined rendering setting, focus setting, or the like.

At 312, method 300 can include detecting, determining, or otherwise receiving a rendering setting to apply to one or more regions of interest. For example, the region of interest can have the same rendering setting as the 2D image slice. In some examples, the 2D image slice and the region of interest can be viewed with a maximum intensity projection (also referred to as MIP), a minimum intensity projection (also referred to as minIP), or an average intensity projection, among others. A user input applied using a 3D cursor to the region of interest can modify the rendering setting within the region of interest to be different from the rendering setting outside of the region of interest. For example, the rendering setting within the region of interest can be modified to be a maximum intensity projection, a minimum intensity projection, or an average intensity projection, among others, while the medical image outside the region of interest may represent the original medical imaging data or native image view without an applied rendering setting. In some examples, a machine learning technique can determine a likelihood of a particular rendering setting to be applied to a selected region of interest and the rendering setting selected by the machine learning technique can be applied. For example, the method 400 can include automatically positioning the three-dimensional cursor with a preselected rendering setting comprising a maximum intensity projection, a minimum intensity projection, or an average intensity projection.

In some examples, the rendering setting is applied within a region of interest and the size of the region of interest is determined or obtained by a user input provided to a user interface with a 3D cursor. For example, the 3D cursor can enable obtained user input selecting a cylindrical region, spherical region, or any other suitable geometrical selection, of a portion of a 3D medical image. The region of interest can include portions of any number of 2D slices from a 3D medical image.

At 314, method 300 can include displaying one or more regions of interest with a different rendering setting than the medical image outside the regions of interest. For example, a region of interest can be displayed with a different focus or zoom setting, a different rendering setting, a different window width or window level, or the like. Window width and window level correspond to the width and center value, respectively, of the range of image intensities for which the image intensities are represented by different grey values on a display device. The different rendering setting of the region of interest can enable visualizing or distinguishing a lung nodule from a blood vessel using a local maximum intensity projection in a chest CT medical image. The different rendering setting of the region of interest can also visualize or distinguish a pulmonary embolism from a surrounding area in a chest CT image using a minimum intensity projection in the region of interest. In some examples, the different rendering setting of the region of interest can also visualize or distinguish a fissure in a bone of a CT medical image using a local average intensity projection of the region of interest.

At 316, method 300 can include detecting, using a 3D cursor, a modification of the location of at least one region of interest. For example, method 300 can include detecting a selection of a region of interest with any suitable mouse click, keyboard selection, or the like. The method 300 can also include detecting a modification of the location of the region of interest with any suitable second user input from a mouse, keyboard, or the like. The second user input can indicate a second location for the region of interest from a drag and drop feature with a user input from a mouse, among others.

In some examples, a number of regions of interest can be obtained or detected and a second user input can cause the modification of the location of one region of interest to move or shift to a second region of interest. For example, a rendering setting of a first region of interest, a size of the first region of interest, a shift of a location of a first region of interest, or a combination thereof can be applied to additional regions of interest in an image.

At 318, method 300 can include adjusting a rendering setting of the second location of the region of interest. In some examples, the second location of the region of interest can be modified to display medical imaging data within the second location of the region of interest with the same rendering setting as the selected region of interest moved to the second location. As discussed in greater detail below in relation to FIGS. 6-9, method 300 enables a user interface to detect, using a 3D cursor, a selection of a region of interest and apply a different rendering setting to the region of interest as the 3D cursor is moved within the user interface providing a 2D data slice of 3D imaging data. In some examples, the region of interest can include one or more of a tumor, sutures, anatomical structures, a medical abnormality, or a combination thereof.

The process flow diagram of method 300 of FIG. 3 is not intended to indicate that all of the operations of blocks 302-318 of the method 300 are to be included in every example. Additionally, the process flow diagram of method 300 of FIG. 3 describes a possible order of executing operations. However, it is to be understood that the operations of the method 300 can be implemented in various orders or sequences. In addition, in some examples, the method 300 can also include fewer or additional operations. For example, the method 300 can also include repositioning the three-dimensional cursor between multiple regions of interest in the 3D medical image in response to a change in a user input. In some examples the user input can cause a 3D cursor to highlight or select different regions of interest in a medical image with any suitable rendering setting.

In some examples, the three-dimensional cursor setting can include adjusting a zoom or focus setting within the region of interest, adjusting the rendering of a lesion in the region of interest, or a combination thereof. In some examples, the method 300 can include obtaining a time series of 3D medical images comprising at least the 3D medical image, and generating the user interface based on the time series of 3D medical images, wherein the three-dimensional cursor enables viewing the rending of the region of interest throughout the time series.

In some examples, the method 300 can include accessing a medical report comprising the 3D medical image, and generating the user interface comprising the 3D medical image with the three-dimensional cursor setting applied inside the region of interest without modifying the medical report. A medical report, as referred to herein, can include any suitable document or set of data that aggregates medical findings in a comprehensive and readable manner for review by a referring physician (prescriber) and, if needed, a medical extended team as part of a multi-disciplinary meeting.

Turning now to FIG. 4, a flowchart illustrating an example method 400 for generating a graphical representation of a region of interest is shown. The method 400 will be described with relation to the systems depicted in FIGS. 1-2, but it should be understood that similar methods may be used with other systems without departing from the scope of this disclosure. The method 400 may be carried out via instructions stored in non-transitory memory of one or more computing devices. In some examples, the method 400 may be carried out by a computing device (e.g., the computing device 200 with processor 202 of FIG. 2) as well as a set of remote servers in communication with the computing device. The computing device may be in communication with an imaging archive (e.g., imaging archive 228).

At 402, the method 400 can include obtaining, detecting, or otherwise receiving a 3D medical image. In some examples, the 3D medical image can include a plurality of images of a 3D multi-volume imaging dataset from the imaging archive. The multi-volume imaging dataset may be acquired via an imaging system (e.g., MRI system 10 of FIG. 1) configured for acquiring multi-volume data, such as multi-parametric imaging data and/or multi-phase imaging data, among others. In some examples, the multi-volume imaging dataset that is to be processed, segmented, and/or rendered may be selected via user input. For example, a user may select a desired multi-volume imaging dataset to be rendered or processed. The user input can also indicate a request that the selected 3D multi-volume imaging dataset be rendered with one or more regions of interest (e.g., by selecting a segmentation tab, tool, or the like).

The 3D multi-volume imaging dataset may include a plurality of image volumes. In some examples, each image volume can be from a different imaging sequence or phase. In some examples, each of the plurality of image volumes may be partitioned into a plurality of 2D slices. Each of the 2D slices may be specific to a particular coordinate according to an axis in which they were obtained (e.g., a z-coordinate for an axial view).

At 404, the method 400 includes displaying an image slice of one or more of the plurality of images in a user interface. In some examples, the displayed image slices may be 2D slices. The user interface can be displayed on a display device (e.g., display device 210 of FIG. 2) and may include one or more selectable elements and/or tools through which the user may interact with the images, render regions of interest in the images, annotate the images, or perform other actions. For example, the user interface can include a 3D cursor that, in response to a selection, can enable navigation of a 3D medical image with additional rendering settings or tools. In some examples, the 3D multi-volume imaging dataset may include images obtained from one or more orientations and therefore images may be displayed in one of various views, e.g., an axial view, sagittal view, coronal view, or the like. In some examples, each of the one or more images displayed may be displayed from the same view.

At 406, the method 400 can include receiving user input of a position of a 3D cursor within a first image slice of the displayed image slices corresponding to the one or more images. In some examples, the first image slice may be of a first image volume representing a 3D medical imaging data set. The 3D cursor may be adjustable via user inputs (e.g., movement of a user input device such as a mouse, trackpad, keyboard, or the like) and the position of the 3D cursor may be determined via user input (e.g., a mouse click, keyboard selection, or the like). In some examples, the position of the 3D cursor can be determined relative to the displayed image/2D slice. In some examples, a coordinate system can be predefined for the 3D imaging data set so that the coordinate system may be the same for each of the volumes of the 3D imaging data set. The position of the 3D cursor can be known, calculated, or otherwise obtained within the first image slice. In some examples, if the coordinate system is the same for each of the volumes, the position of the 3D cursor can be transposed to the other of the plurality of images.

At 408, method 400 can include obtaining, defining, or otherwise determining a size and rendering setting of a region of interest. The size can indicate a geometrical shape in two dimensional or three dimensional space to select representing the region of interest in the 3D medical image. For example, the size of the region of interest can indicate a size of a circular 2D area in a 2D image, a size of a cylindrical 3D area within multiple 2D images of a 3D image, or any other suitable 2D or 3D selection. In some examples, a first region of interest can be a cylindrical 3D selection and a second region of interest can be a rectangular prism 3D selection within a 3D image. Any other suitable geometrical shapes can be used to define or identify one or more regions of interest in a medical image. For example, any suitable 3D geometrical shape can be used to capture regions of interest along a depth or z-axis in a 3D medical image.

As discussed above, the rendering setting can indicate a maximum projection intensity, a minimum projection intensity, or an average projection intensity based on the size of the region of interest. For example, the rendering setting can be applied to any suitable number of pixels or voxels within a region of interest to provide a different sampling of regions or portions of a 3D medical image. In some examples, the region of interest is a portion of an artery and the method 400 can include providing, using the user interface, a visualization of stenosis in the portion of the artery.

At 410, the method 400 can include generating a graphical representation of the region of interest. In some examples, the graphical representation of the region of interest can include detecting a signal intensity of pixels or voxels in a region of interest over time based on the rendering setting. The graphical representation can indicate an average intensity of the pixels or voxels of the region of interest, among other characteristics. In some examples, method 400 can include detecting or obtaining a larger selection of pixels or voxels from the region of interest to reduce an excessive amount of variability in intensity of selected pixels or voxels. The graphical representation of the region of interest can represent a change in intensity of pixels or voxels at any suitable time interval based on a time series of 3D medical images capturing the region of interest. For example, the graphical representation can depict a change in intensity of pixels or voxels within a second, a minute, an hour, or any other suitable time interval.

At 412, the method 400 can include displaying the graphical representation of the region of interest in a user interface. In some examples, the graphical representation can be displayed proximate to a 2D slice of 3D medical imaging data, in a separate user interface, or the like. The graphical representation can indicate any number of different abnormalities in a medical image. For example, the graphical representation can provide a plotting of a baseline curve representing contrast agent uptake in the myocardium of a patient. In some examples, because of respiratory and cardiac motion, signal at the voxel level can be noisy or highly variable. The signal at the voxel level can also be noisy or highly variable due to medical image acquisition modality specificities, but also image acquisition and reconstruction parameters. The graphical representation using a rendering setting applied to a region of interest can enable the generation of an averaging signal with a less volatile curve. The graphical representation of the intensity of pixels or voxels in a region of interest can be compared to a graphical representation obtained from a region of interest deposited in a breast tumor to identify, characterize, or detect a breast tumor abnormality in a medical image of a patient. In some examples, the graphical representation of the intensity of pixels or voxels in a region of interest can indicate any lesion in any organ.

The process flow diagram of method 400 of FIG. 4 is not intended to indicate that all of the operations of blocks 402-412 of the method 400 are to be included in every example. Additionally, the process flow diagram of method 400 of FIG. 4 describes a possible order of executing operations. However, it is to be understood that the operations of the method 400 can be implemented in various orders or sequences. In addition, in some examples, the method 400 can also include fewer or additional operations. In some examples, the method 400 can include navigating one or more 3D medical images using the user interface and the three-dimensional cursor setting.

Turning now to FIG. 5, an example image from a multi-volume imaging dataset of a patient is shown. The multi-volume imaging dataset may be a multi-parametric imaging dataset that includes a plurality of image volumes from various imaging sequences. For example, the first multi-volume imaging dataset may be any suitable multi-parametric MRI scan of an anatomical region of a patient.

The multi-volume imaging dataset may include an image 502 of a first volume that includes a plurality of images, or 2D slices. The image 502 may include data of the same anatomy of the patient as any number of additional 2D slices. In some examples, regions of interest 504 and 506 can be included in the image 502. The regions of interest 504 and 506 can be a lesion, a tumor, a region of an organ, or other features present in a volume of medical images.

In some examples, the multi-volume imaging dataset with 3D imaging data can include a first volume that may be of a T1 weighted sequence, a second volume that may be of a T1 weighted contrast enhanced sequence, and a third volume that may be of a FLAIR sequence. Additional sequences may be included in the multi-volume imaging dataset not shown here. Each of the sequences of the multi-volume imaging dataset may be acquired by an imaging system during a single scan acquisition. Therefore, the regions of interest 504 and 506 can be imaged through each of the sequences during the same period of time.

Each of the sequences of the multi-volume imaging dataset may focus, highlight, or otherwise show different parts of the anatomy that is imaged. For example, the T1 weighted contrast enhanced sequence may show areas of enhancement more than the T1 weighted sequence. In this way, the regions of interest 504 and 506 may be viewed with multiple parameters, providing increased information about the region of interest which may be used to more accurately separate the regions of interest from surrounding anatomy.

The volume of imaging dataset may include a plurality of 2D or 3D medical images, wherein 502 is one of the images. In some examples, multiple volumes of imaging data can be obtained. A first volume may be a first phase, such as a non-contrasted phase, a second volume may be of a second phase, such as an arterial phase, a third volume may be of a third phase, such as a portal venous phase, and a fourth volume may be of a fourth phase, such as a delayed phase, among others. The phases may be obtained at varying times during scan acquisition, in some examples as a contrast agent travels through vasculature. In some examples, each of the volumes can include data of the same regions of interest, such as region of interest 504 and 506. The regions of interest 504 and 506 may appear differently in each of the volumes due to the different phases. In this way, additional information about the regions of interest 504 and 506 may be determined.

In some examples, each region of interest 504 and 506 can capture a three-dimensional segment or portion of data from a 3D medical image using the same or different geometrical shape or identifiers. For example, the region of interest 504 can identify or obtain intensity data for pixels or voxels within a region of interest defined with a cylindrical region. In other examples, the region of interest 506 can identify or obtain intensity data for pixels or voxels within a region of interest defined with a rectangular prism region. In some examples, a rendering setting can be applied to each region of interest, wherein the rendering setting may be shared or different. For example, the regions of interest 504 and 506 can detect intensity data using a shared or different rendering setting, such as a maximum intensity projection for each pixel or voxel, a minimum intensity projection for each pixel or voxel, or an average intensity projection for each pixel or voxel.

Figure 6:
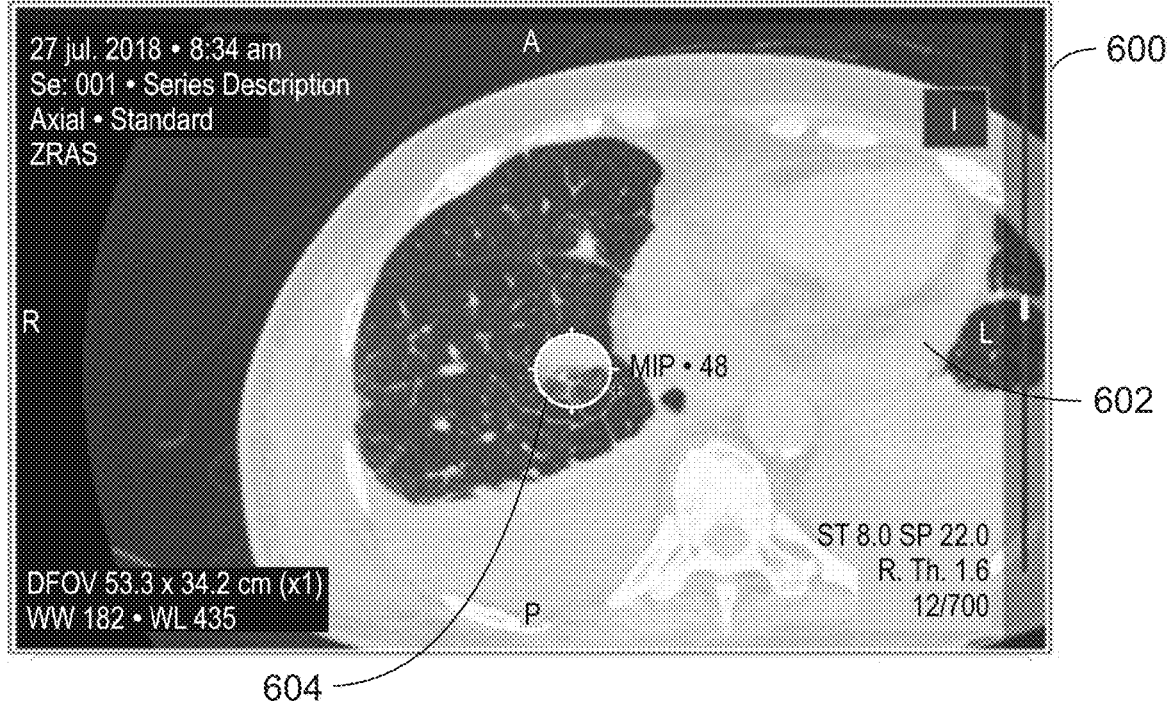
FIG. 6 shows an example image of a user interface for rendering medical images according to an example of the disclosure.

Turning now to FIGS. 6, an example user interface 600 is shown. The user interface 600 may be displayed on a display device, such as display device 210 of FIG. 2, in communication with an image processing system, such as computing device 200 of FIG. 2. The user interface 600 may display one or more images of a multi-volume imaging dataset of a patient acquired by an imaging system and stored within an imaging archive, such as imaging archive 228, which is in communication with the computing device 200.

In some examples, the user interface 600 can display any number of images of an imaging dataset. For example, the user interface 600 can display a first image 602 and any number of additional images. In some examples, the first image 602 can belong to any suitable volume of an imaging dataset and additional images provided or displayed by the user interface 600 can belong to a shared or different imaging dataset. Different volumes of medical imaging data can be from different sequences or different phases. For example, a region of interest 604 may be imaged in each of the volumes. In some examples, the user interface 600 may display one image slice (e.g., 2D slice) of a respective image volume at a time.

In some examples, the user interface 600 can include a 3D cursor 604 to enable selecting regions of interest in available sequences or phases of a multi-volume imaging dataset. The user interface 600 may further include a plurality of tool icons (not depicted) that, when selected via user input, launch a corresponding tool, such as a ruler tool, a brightness adjustment tool, a segmentation tool, and the like through which a user may interact with the one or more images.

In some examples, the user interface 600 can provide any suitable intensity projection statistics for a region of interest, such as an average projection intensity, a maximum projection intensity, or a minimum projection intensity, among others. The user interface 600 can also provide measurement data for a region of interest indicating a diameter of a region of interest, a distance between two or more point of interest within the region of interest, a volume of a region of interest, or the like. For example, generating the user interface 600 can include generating a measurement tool to provide one or more measurements captured within the region of interest with the applied three-dimensional cursor setting. In some examples, images for multi-volume imaging datasets may be acquired by an imaging system, stored in an imaging archive, and displayed within the user interface 600.

Figure 7:
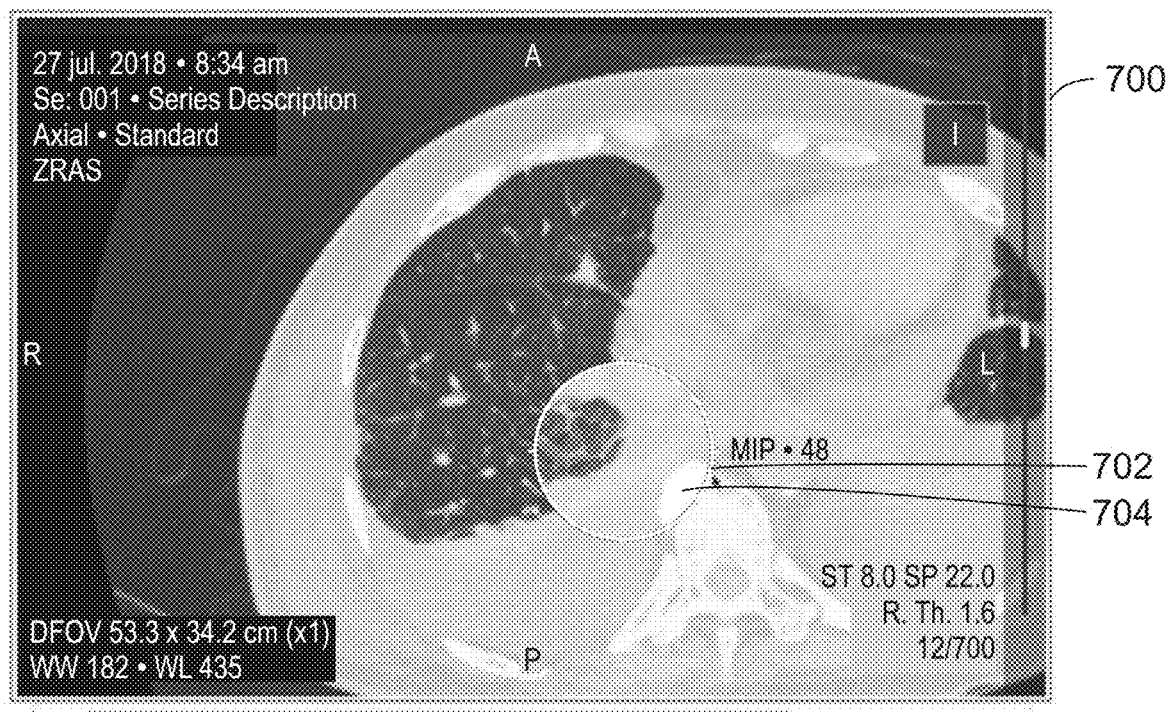
FIG. 7 shows an example image of a user interface for rendering medical images with an adjusted region of interest radius according to an example of the disclosure.

Turning now to FIG. 7, an example user interface 700 for rendering medical images with an adjusted region of interest radius is shown. The user interface 700 may be displayed on a display device, such as display device 210 of FIG. 2, in communication with an image processing system, such as computing device 200 of FIG. 2. The user interface 700 may display one or more images of a multi-volume imaging dataset of a patient acquired by an imaging system and stored within an imaging archive, such as imaging archive 228, which is in communication with the computing device 200.

In the user interface 700, the region of interest 604 can be selected with a 3D cursor 702. The 3D cursor 702 can provide a feature to modify the size of the region of interest 604. In the example of FIG. 7, the region of interest 604 is enlarged, using the 3D cursor 702, to identify a new region of interest 704. In some examples, the 3D cursor can also provide features that can modify additional settings of the region of interest 704, such as the rendering setting, the focus setting, a measurement tool, or the like. In some examples, a maximum intensity projection, a minimum intensity projection, and an average intensity projection are based on two or more two-dimensional portions of a cylindrical region in the 3D medical image.

Figure 8:
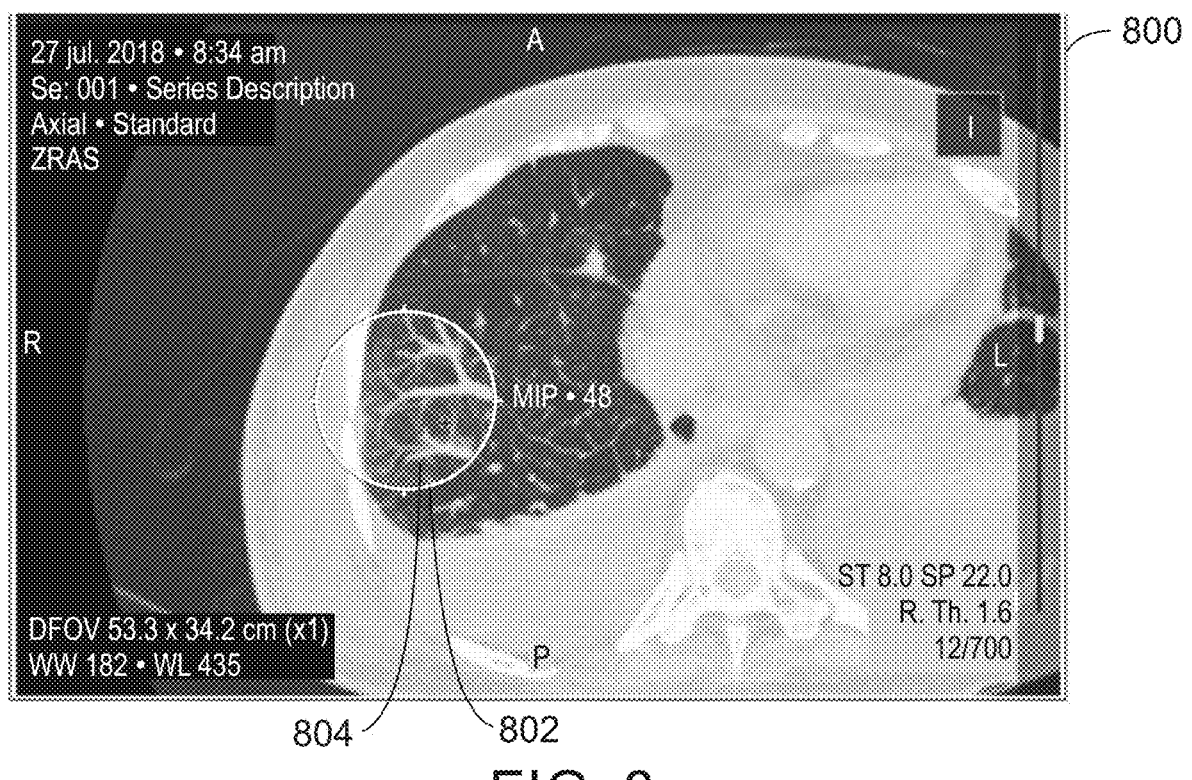
FIG. 8 shows an example image of a user interface for rendering medical images with an adjusted region of interest position according to an example of the disclosure.

Turning now to FIG. 8, an example user interface 800 for rendering medical images with an adjusted region of interest position is shown. The user interface 800 may be displayed on a display device, such as display device 210 of FIG. 2, in communication with an image processing system, such as computing device 200 of FIG. 2. The user interface 800 may display one or more images of a multi-volume imaging dataset of a patient acquired by an imaging system and stored within an imaging archive, such as imaging archive 228, which is in communication with the computing device 200.

The user interface 800 depicts a movement of the region of interest 704 after selection with a 3D cursor 802. The 3D cursor 802 can provide a feature to move the region of interest 704 to a second region of interest 804. In some examples, the 3D cursor 802 can enable moving the region of interest 704 to any suitable portion of a medical image displayed in the user interface 800. The user interface 800 can support any user input from a mouse, keyboard, trackpad, or combination thereof. The user input can move the region of interest 704 to the second region of interest 804 with a drag and drop operation, or the like. The rendering setting of the region of interest 804 is automatically adjusted in real-time or in near real-time using the rendering setting of the region of interest 704. The first region of interest 704 is returned to the same rendering setting as the surrounding medical image.

Figure 9:
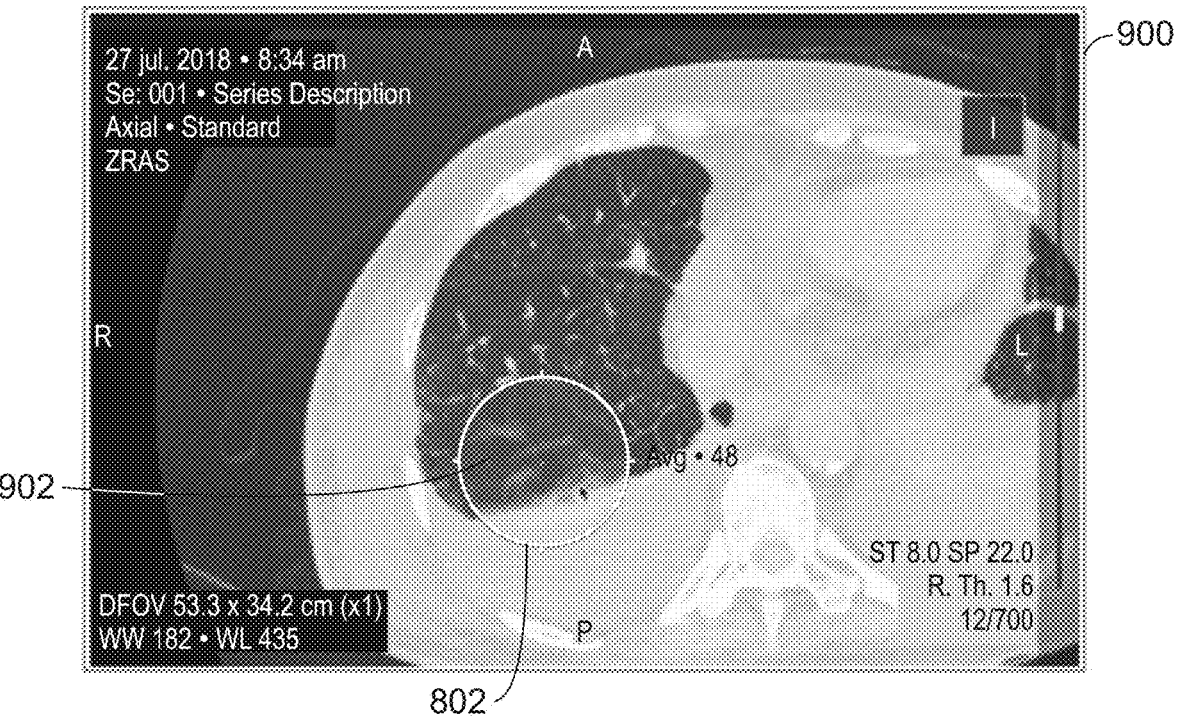
FIG. 9 shows an example image of a user interface for rendering medical images with an adjusted region of interest position and a different local rendering inside the region of interest according to an example of the disclosure.
Figure 10A:
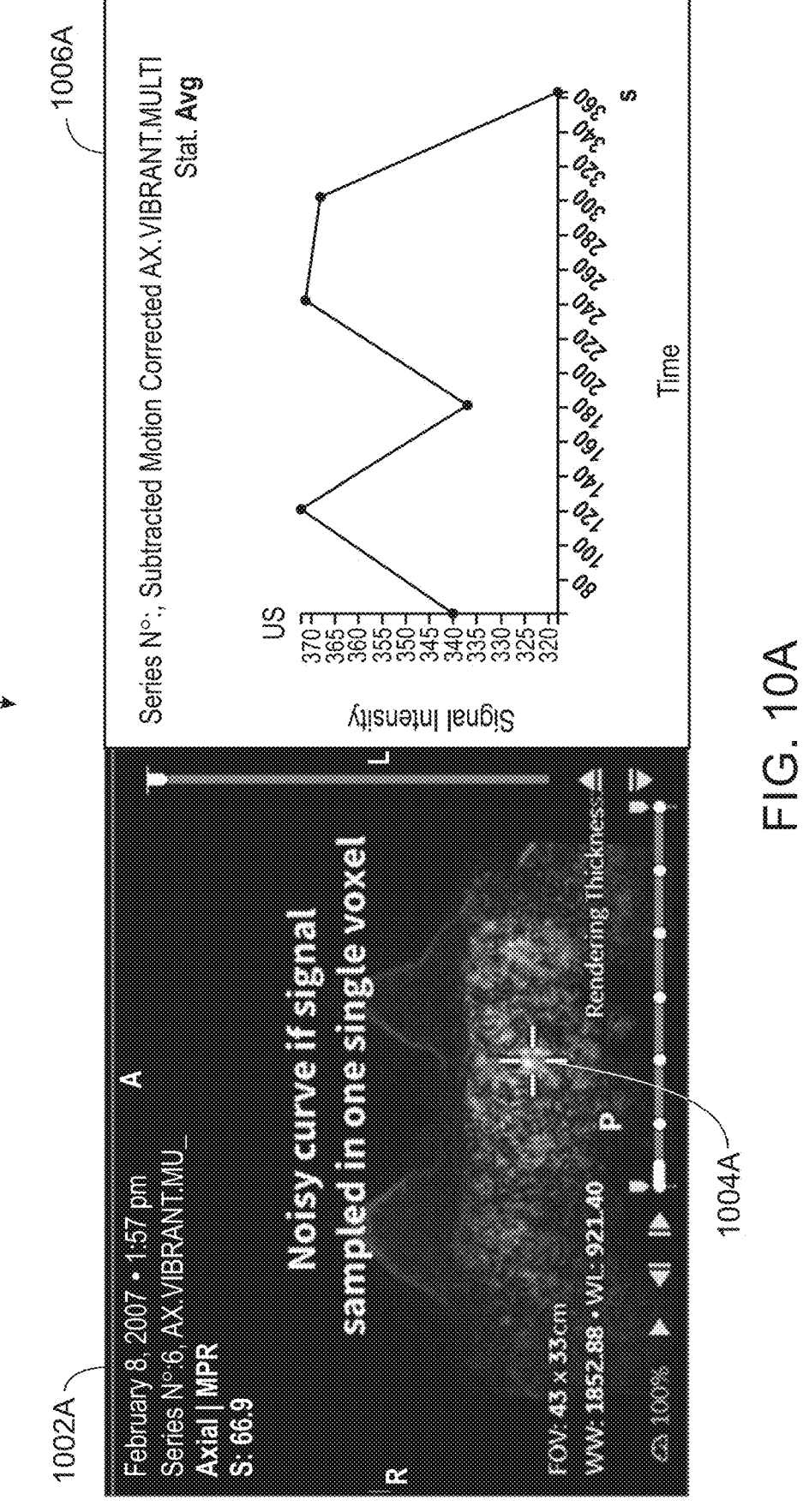
FIGS. 10A and 10B depict graphical representations of medical imaging data from a region of interest according to an example of the disclosure.
Figure 10B:
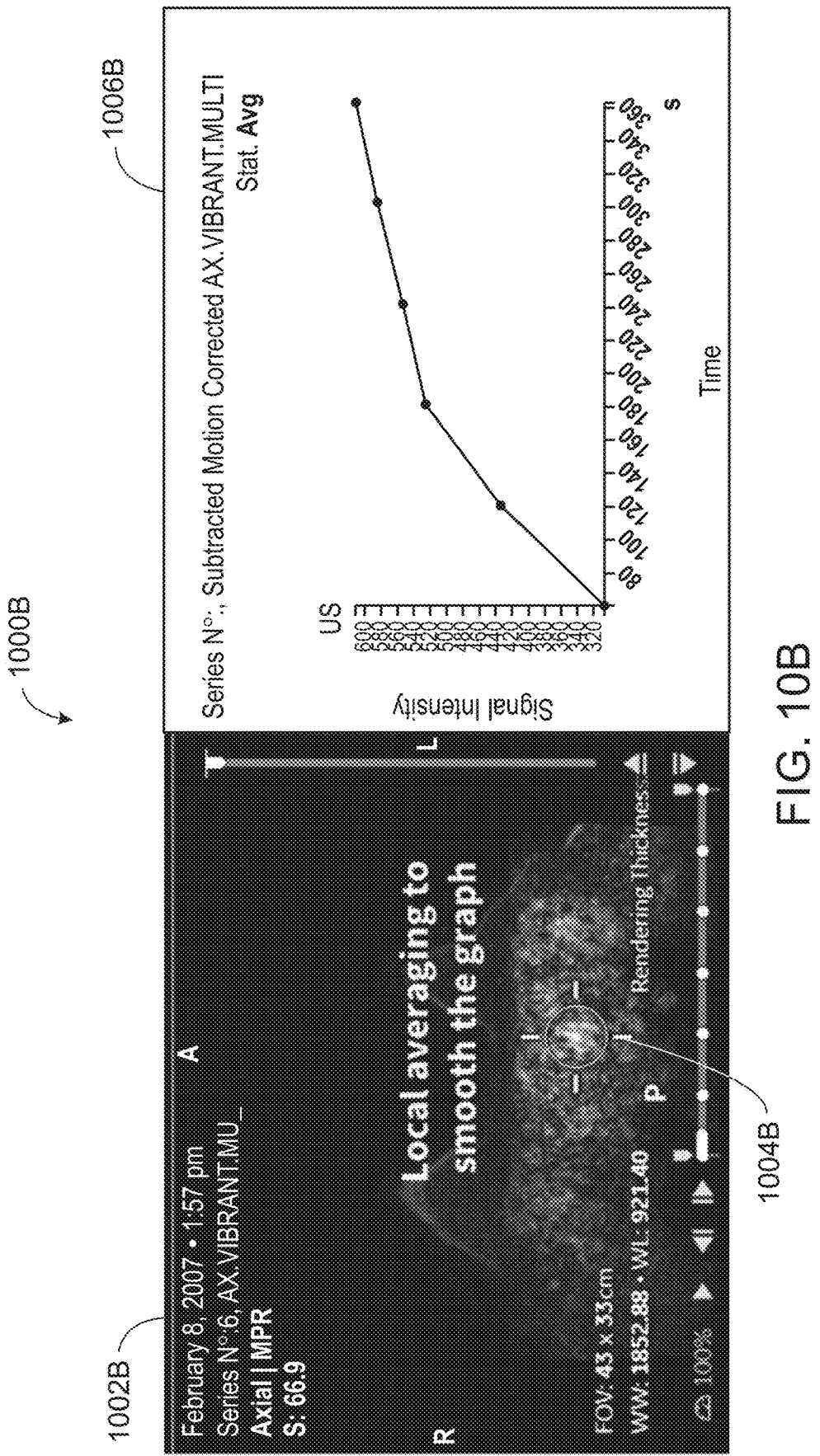

Turning now to FIG. 9, an example user interface 900 for rendering medical images with an adjusted region of interest position and a different local rendering inside the region of interest is shown. The user interface 900 may be displayed on a display device, such as display device 210 of FIG. 2, in communication with an image processing system, such as computing device 200 of FIG. 2. The user interface 900 may display one or more images of a multi-volume imaging dataset of a patient acquired by an imaging system and stored within an imaging archive, such as imaging archive 228, which is in communication with the computing device 200.

In the user interface 900, the region of interest 804 can be selected with a 3D cursor 802 and moved to a new region of interest 902. Additionally, the 3D cursor 802 can provide a new rendering setting for the region of interest 902. For example, the 3D cursor 802 can enable changing the maximum intensity projection of region of interest 804 to an average intensity projection. In some examples, the 3D cursor 802 can also enable changing the intensity projection to a minimum intensity projection, among others. Furthermore, the 3D cursor 802 can also enable modifying additional rendering settings such as a different focus or zoom setting, a different window width or window level, among others.

Turning to FIGS. 10A and 10B, graphical representations of intensity signals in regions of interest in medical imaging data are depicted. The user interfaces 1000A of FIGS. 10A and 1000B of FIG. 10B may be displayed on a display device, such as display device 210 of FIG. 2, in communication with an image processing system, such as computing device 200 of FIG. 2. The user interfaces 1000A and 1000B may display one or more images of a multi-volume imaging dataset of a patient acquired by an imaging system and stored within an imaging archive, such as imaging archive 228, which is in communication with the computing device 200.

In some examples, the user interface 1000A of FIG. 10A can display a medical image 1002A along with a cursor 1004A. The cursor 1004A can select a pixel or voxel from the medical image 1002A. In some examples, the user interface 1000A can generate a graphical representation 1006A of the signal intensity of the selected pixel or voxel over time. The graphical representation 1006A can include a significant amount of variability due to a single pixel or voxel being monitored over time for the signal intensity.

In some examples, the user interface 1000B can display a medical image 1002B along with a 3D cursor 1004B. The 3D cursor 1004B can select a group of pixels or voxels from the medical image 1002B. In some examples, the user interface 1000B can generate a graphical representation

1006B of the signal intensity of the selected group of pixels or voxels over time. The graphical representation 1006B can reduce an amount of variability in a signal intensity for the selected group of pixels or voxels due to a larger sample size.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system for rendering medical images comprising:
a processor configured to:
obtain, using a three-dimensional cursor, a selection of a region of interest from a three-dimensional (3D) medical image;
detect a three-dimensional cursor setting for the region of interest, the three-dimensional cursor setting indicating at least a rendering setting for the region of interest; and
modify a user interface comprising the 3D medical image with the three-dimensional cursor setting applied inside the region of interest, wherein movement of the three-dimensional cursor causes a selection of a second region in the 3D medical image, wherein the second region is displayed with the rendering setting, wherein the processor is further configured to render and segment additional regions of interest across multiple image volumes of multiparametric or multi-phase imaging data, wherein one or more geometrical shapes are used to segment the additional regions of interest.

2. The system of claim 1, wherein the processor is further configured to reposition the three-dimensional cursor between multiple regions of interest in the 3D medical image in response to a change in a user input.

3. The system of claim 1, wherein the processor is to automatically position the three-dimensional cursor at the region of interest with a predetermined depth, wherein the region of interest represents a cylindrical region in the 3D medical image.

4. The system of claim 3, wherein the processor is to automatically position the three-dimensional cursor with a preselected rendering setting comprising a maximum intensity projection, a minimum intensity projection, or an average intensity projection, a preselected window width and window level, a preselected zoom setting, or a combination thereof.

5. The system of claim 4, wherein the maximum intensity projection, the minimum intensity projection, and the average intensity projection are based on two or more two-dimensional portions of the cylindrical region in the 3D medical image.

6. The system of claim 1, wherein the processor is to generate a measurement tool to provide one or more measurements captured within the region of interest with the applied three-dimensional cursor setting.

7. The system of claim 1, wherein the region of interest comprises one or more of a lesion, anatomical structures, or a combination thereof.

8. The system of claim 1, wherein the three-dimensional cursor setting comprises adjusting a focus setting within the region of interest, adjusting the rendering of a lesion in the region of interest, or a combination thereof.

9. The system of claim 1, wherein the processor is to:
obtain a time series of 3D medical images comprising at least the 3D medical image; and
generate the user interface based on the time series of 3D medical images, wherein the three-dimensional cursor enables viewing the rending of the region of interest throughout the time series.

10. The system of claim 1, wherein the processor is to:
access a medical report comprising the 3D medical image; and
generate the user interface comprising the 3D medical image with the three-dimensional cursor setting applied inside the region of interest without modifying the medical report.

11. The system of claim 1, wherein the region of interest is a portion of an artery and the processor is to provide, using the user interface, a visualization of stenosis in the portion of the artery.

12. The system of claim 1, wherein the region of interest is a cylindrical region within the 3D medical image.

13. The system of claim 12, wherein the processor is to generate a graph based on an intensity associated with the rendering setting applied within the region of interest, wherein the region of interest comprises a plurality of voxels from the 3D medical image, and wherein the intensity is measured over time.

14. The system of claim 1, wherein the processor is to navigate one or more 3D medical images using the user interface and the three-dimensional cursor setting.

15. A method for rendering medical images comprising:
obtaining, using a three-dimensional cursor, a selection of a region of interest from a three-dimensional (3D) medical image;
detecting a three-dimensional cursor setting for the region of interest, the three-dimensional cursor setting indicating at least a rendering setting for the region of interest; and modifying a user interface comprising the 3D medical image with the three-dimensional cursor setting applied inside the region of interest, wherein movement of the three-dimensional cursor causes a selection of a second region in the 3D medical image, wherein the second region is displayed with the rendering setting, wherein additional regions of interest across multiple image volumes of multi-parametric or multi-phase imaging data are rendered and segmented, wherein one or more geometrical shapes are used to segment the additional regions of interest.

16. The method of claim 15, further comprising repositioning the three-dimensional cursor between multiple regions of interest in the 3D medical image in response to a change in a user input.

17. The method of claim 15, further comprising automatically positioning the three-dimensional cursor at the region of interest with a predetermined depth, wherein the region of interest represents a cylindrical region in the 3D medical image.

18. The method of claim 17, further comprising automatically positioning the three-dimensional cursor with a preselected rendering setting comprising a maximum intensity projection (MIP), a minimum intensity projection (minIP), or an average intensity projection.

19. The method of claim 18, wherein the maximum intensity projection (MIP), the minimum intensity projection (minIP), and the average intensity projection are based on two or more two-dimensional portions of the cylindrical region in the 3D medical image.

20. A non-transitory computer readable medium for rendering medical images comprising a plurality of instructions that, in response to execution by a processor, cause the processor to:
obtain, using a three-dimensional cursor, a selection of a region of interest from a three-dimensional (3D) medical image;
detect a three-dimensional cursor setting for the region of interest, the three-dimensional cursor setting indicating at least a rendering setting for the region of interest, the rendering setting comprising a maximum intensity projection, a minimum intensity projection, or an average intensity projection; and
modify a user interface comprising the 3D medical image with the three-dimensional cursor setting applied inside the region of interest, wherein movement of the three-dimensional cursor causes a selection of a second region in the 3D medical image, wherein the second region is a cylindrical selection displayed with the rendering setting, wherein the processor is further configured to render and segment additional regions of interest across multiple image volumes of multi-parametric or multi-phase imaging data, wherein one or more geometrical shapes are used to segment the additional regions of interest.

* * * * *